United States Patent [19]

Collins et al.

[11] Patent Number: 4,647,569

[45] Date of Patent: Mar. 3, 1987

[54] ANTIARTHRITIC PYRIDYLAMINOETHENE DISULFONYL COMPOUNDS AND USE

[75] Inventors: Raymond F. Collins, Harold Wood; Philip Knowles, Rayleigh; Libert C. Saunders, Grays; Francis J. Tierney, Stepney; Peter J. Warne, London, all of England

[73] Assignee: May & Baker Limited, Essex, England

[21] Appl. No.: 777,866

[22] Filed: Sep. 19, 1985

Related U.S. Application Data

[63] Continuation of Ser. No. 707,528, Mar. 4, 1985, abandoned, which is a continuation of Ser. No. 587,969, Mar. 9, 1984, abandoned.

[30] Foreign Application Priority Data

Mar. 11, 1983 [GB] United Kingdom ............... 8306755

[51] Int. Cl.$^4$ ............... C07D 213/74; C07D 213/84; C07D 213/79; A61K 31/44
[52] U.S. Cl. ..................... 514/340; 514/346; 514/344; 514/348; 514/347; 514/349; 514/352; 546/276; 546/287; 546/288; 546/289; 546/291; 546/292; 546/293; 546/294; 546/295; 546/296; 546/297; 546/305; 546/307; 546/308; 546/309; 546/310; 546/312
[58] Field of Search ............... 546/312, 296, 307, 297, 546/286, 308, 287, 309, 288, 293, 289, 291, 292, 310, 276, 294, 295, 305; 514/352, 340, 344, 346, 348, 347, 349

[56] References Cited

U.S. PATENT DOCUMENTS 4,013,656 3/1977 Ackermann et al. ............... 546/312

OTHER PUBLICATIONS

Golds, et al. Arthritis and Rheumatism, vol. 26, No. 1 (Jan. 1983), pp. 15–21.
Janossy, G. et al. The Lancet, Oct. 17, 1981, pp. 839–842.
Baker, D. G. et al. Arthritis and Rheumatism, vol. 26, No. 1 (Jan. 1983), pp. 8–14.

*Primary Examiner*—Henry R. Jiles
*Assistant Examiner*—Dale A. Bjorkman
*Attorney, Agent, or Firm*—Stevens, Davis, Miller & Mosher

[57] ABSTRACT

Pyridylaminoethene derivatives of the formula:

$$R^1NHCH=C\underset{SO_2R^3}{\overset{SO_2R^2}{\diagup}} \qquad I$$

wherein $R^1$ is pyridyl, unsubstituted or substituted by one or more substituents $R^4$ selected from halogen, amino, carboxy, cyano nitro, hydroxy, formyl, trifluoromethyl, aryl, aryloxy, arylthio, benzyloxycarbonylamino, sulphamoyl, tetrazol-5-yl, carbamoyl, thiocarbamoyl, arylcarbamoyl, aroyl, alkyl, alkoxy, alkylthio, alkylsulphonyl, alkylamino, alkylsulphamoyl, arylalkyl, alkanoyl, alkoxycarbonyl, alkoxycarbonylamino, alkylcarbamoyl, alkanoylamino, N-benzyloxycarbonyl-N-alkylamino, or dialkylsulphamoyl, dialkylamino or dialkylcarbamoyl, wherein the alkyl groups may together form a ring, and $R^2$ and $R^3$ each represents phenyl, unsubstituted or substituted by one or more substituents $R^4$ as hereinbefore defined, possess antiarthritic properties.

23 Claims, No Drawings

ANTIARTHRITIC PYRIDYLAMINOETHENE DISULFONYL COMPOUNDS AND USE

This application is a continuation of application Ser. No. 707,528, filed 3/4/85, abandoned, which in turn is a continuation of application Ser. No. 587,969 filed 3/9/84, abandoned.

This invention relates to new therapeutically useful pyridylaminoethene derivatives, to a process for their preparation, to pharmaceutical compositions containing them, and to their use as pharmaceuticals.

The new pyridylaminoethene compounds are compounds of the general formula:

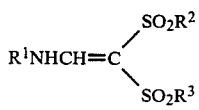

I wherein $R^1$ represents a pyridyl group, preferably a pyrid-2-yl group, which is unsubstituted or substituted by one or more substituents $R^4$ [which may be the same or different and each represents a halogen (i.e. fluorine, chlorine, bromine or iodine) atom or an amino, carboxy, cyano, nitro, hydroxy, formyl, trifluoromethyl, aryl, aryloxy, arylthio, benzyloxycarbonylamino, sulphamoyl, tetrazol-5-yl, carbamoyl, thiocarbamoyl, arylcarbamoyl or aroyl group, or a straight- or branched-chain alkyl group containing from 1 to 6 carbon atoms, or a straight- or branched-chain alkoxy, alkylthio, alkylsulphonyl, alkylamino, alkylsulphamoyl or arylalkyl group containing from 1 to 6 carbon atoms in the alkyl moiety, a straight- or branched-chain alkanoyl, alkoxycarbonyl, alkoxycarbonylamino, alkylcarbamoyl or alkanoylamino group containing from 2 to 6 carbon atoms, an N-benzyloxycarbonyl-N-alkylamino group wherein the alkylamino moiety is straight- or branched-chain and contains from 1 to 6 carbon atoms, or a dialkylsulphinyl, dialkylamino or dialkylcarbamoyl group wherein the alkyl moieties may be straight or branched and may each contain from 1 to 6 carbon atoms and may be linked together to form a ring preferably a 5- to 9-membered ring] and $R^2$ and $R^3$ may be the same or different and each represents a phenyl group which may be unsubstituted or substituted by one or more substituents $R^4$ (as hereinbefore defined).

Aryl groups and moieties and aroyl groups within the definition of $R^4$ are, for example, phenyl or benzoyl groups bearing one or more substituents, for example substituents selected from those listed above in the definition of $R^4$.

The substituents $R^4$ may be the same or different.

Preferred values of $R^1$ include pyridyl and pyridyl substituted by 4 or 2 substituents $R^4$ or, preferably, 1 substituent $R^4$.

Preferred values of $R^4$ include halogen (e.g. chlorine, bromine or iodine) atoms and amino, cyano, nitro, trifluoromethyl, aryl (e.g. phenyl), arylthio (e.g. phenylthio), sulphamoyl, carbamoyl, thiocarbamoyl, arylcarbamoyl (e.g., phenylcarbamoyl), alkyl (e.g. methyl or butyl), alkylsulphamoyl (e.g. methylsulphamoyl), arylalkyl (e.g. benzyl), alkoxycarbonyl (e.g. methoxycarbonyl), alkylcarbamoyl (e.g. methylcarbamoyl or butylcarbamoyl), dialkylsulphamoyl (e.g. diethylsulphamoyl), dialkylamino (e.g. dimethylamino or piperidino) and dialkylcarbamoyl (e.g. diethylcarbamoyl, diisopropylcarbamoyl or piperidinocarbonyl) groups.

Preferred values of $R^2$ and $R^3$ include unsubstituted phenyl groups and phenyl groups each substituted by a halogen (e.g. chlorine) atom or by an alkyl (e.g. methyl), alkoxy (e.g. methoxy), nitro or trifluoromethyl group.

When $R^2$ and $R^3$ are different, this specification is intended to embrace the E-form and the Z-form, which arise as a result of geometrical isomerism, and mixtures thereof.

Especially important compounds of formula I are as follows:

| | |
|---|---|
| 1,1-bis(phenylsulphonyl)-2-(5-bromopyrid-2-ylamino)ethene; | A |
| 1,1-bis(phenylsulphonyl)-2-(pyrid-2-ylamino)ethene; | B |
| 1,1-bis(phenylsulphonyl)-2-(5-iodopyrid-2-ylamino)ethene; | C |
| 1,1-bis(phenylsulphonyl)-2-(5-dimethylaminopyrid-2-ylamino)ethene; | D |
| 1,1-bis(phenylsulphonyl)-2-(5-piperidinopyrid-2-ylamino)ethene; | E |
| 1,1-bis(phenylsulphonyl)-2-(5-nitropyrid-2-ylamino)ethene; | F |
| 1,1-bis(phenylsulphonyl)-2-(5-butylpyrid-2-ylamino)ethene; | G |
| 1,1-bis(phenylsulphonyl)-2-(5-cyanopyrid-2-ylamino)ethene; | H |
| 1,1-bis(phenylsulphonyl)-2-(5-methoxycarbonylpyrid-2-ylamino)ethene; | I |
| 1,1-bis(phenylsulphonyl)-2-(5-carbamoylpyrid-2-ylamino)ethene; | J |
| 2-(5-aminopyrid-2-ylamino)-1,1-bis(phenylsulphonyl)ethene; | K |
| 2-(5-bromopyrid-2-ylamino)-1-(3-chlorophenylsulphonyl)-1-phenylsulphonylethene; | L |
| 2-(5-bromopyrid-2-ylamino)-1-phenylsulphonyl-1-(3-trifluoromethylphenylsulphonyl)ethene; | M |
| 2-(5-bromopyrid-2-ylamino)-1-(3-nitrophenylsulphonyl)-1-phenylsulphonylethene; | N |
| 2-(5-bromopyrid-2-ylamino)-1-(3-methoxyphenylsulphonyl)-1-phenylsulphonylethene; | O |
| 2-(5-bromopyrid-2-ylamino)-1-(3-methylphenylsulphonyl)-1-phenylsulphonylethene; | P |
| 2-(5-bromopyrid-2-ylamino)-1-(2-methoxyphenylsulphonyl)-1-phenylsulphonylethene; | Q |
| 2-(5-bromopyrid-2-ylamino)-1-(2-chlorophenylsulphonyl)-1-phenylsulphonylethene; | R |
| 2-(5-bromopyrid-2-ylamino)-1-(2-methylphenylsulphonyl)-1-phenylsulphonylethene; | S |
| 2-(5-bromopyrid-2-ylamino)-1,1-bis(3-nitrophenylsulphonyl)ethene; | T |
| 2-(5-bromopyrid-2-ylamino)-1,1-bis(4-chlorophenylsulphonyl)ethene; | U |
| 2-(5-bromopyrid-2-ylamino)-1,1-bis(4-methoxyphenylsulphonyl)ethene; | V |
| 2-(5-bromopyrid-2-ylamino)-1,1-bis(4-methylphenylsulphonyl)ethene; | W |
| 2-(5-bromopyrid-2-ylamino)-1-(4-chlorophenylsulphonyl)-1-phenylsulphonylethene; | X |
| 2-(5-bromopyrid-2-ylamino)-1-(4-methylphenylsulphonyl)-1-phenylsulphonylethene; | Y |
| 2-(5-bromopyrid-2-ylamino)-1-(4-methoxyphenylsulphonyl)-1-phenylsulphonylethene; | Z |
| 2-(6-methyl-5-nitropyrid-2-ylamino)-1,1-bis(phenylsulphonyl)ethene; | AA |
| 2-(4-methyl-3-nitropyrid-2-ylamino)-1,1-bis(phenylsulphonyl)ethene; | BB |
| 2-(2-chloropyrid-3-ylamino)-1,1-bis(phenylsulphonyl)ethene; | CC |
| 1,1-bis(phenylsulphonyl)-2-(5-sulphamoylpyrid-2-ylamino)ethene; | DD |
| 2-(5-N,N—diethylsulphamoylpyrid-2-ylamino)-1,1-bis(phenylsulphonyl)ethene; | EE |
| 2-(5-N—methylsulphamoylpyrid-2-ylamino)-1,1-bis(phenylsulphonyl)ethene; | FF |
| 2-(5-N,N—diisopropylcarbamoylpyrid-2-ylamino)-1,1-bis(phenylsulphonyl)ethene; | GG |

-continued

| | |
|---|---|
| 2-(5-thiocarbamoylpyrid-2-ylamino)-1,1-bis-(phenylsulphonyl)ethene; | HH |
| 2-(5-N,N—diethylcarbamoylpyrid-2-ylamino)-1,1-bis(phenylsulphonyl)ethene; | II |
| 2-(5-N—butylcarbamoylpyrid-2-ylamino)-1,1-bis(phenylsulphonyl)ethene; | JJ |
| 2-(5-N—methylcarbamoylpyrid-2-ylamino)-1,1-bis-(phenylsulphonyl)ethene; | KK |
| 1,1-bis(phenylsulphonyl)-2-(5-N—phenyl-carbamoylpyrid-2-ylamino)ethene; | LL |
| 1,1-bis(phenylsulphonyl)-2-(5-piperidino-carbonylpyrid-2-ylamino)ethene; | MM |
| 2-(4-methylpyrid-2-ylamino)-1,1-bis(phenyl-sulphonyl)ethene; | NN |
| 2-(6-methylpyrid-2-ylamino)-1,1-bis(phenyl-sulphonyl)ethene; | OO |
| 2-(4-methylpyrid-3-ylamino)-1,1-bis(phenyl-sulphonyl)ethene; | PP |
| 1,1-bis(phenylsulphonyl)-2-(5-phenylthio-pyrid-2-ylamino)ethene; | QQ |
| 2-(5-carbamoylpyrid-3-ylamino)-1,1-bis-(phenylsulphonyl)ethene; | RR |
| 2-(4-benzylpyrid-2-ylamino)-1,1-bis(phenyl-sulphonyl)ethene; | SS |
| 2-(6-benzylpyrid-2-ylamino)-1,1-bis(phenyl-sulphonyl)ethene; | TT |
| 1,1-bis(phenylsulphonyl)-2-(2-phenylthio-pyrid-3-ylamino)ethene; | UU |
| 2-(5-carbamoyl-6-chloro-4-methyl-3-phenyl-pyrid-2-ylamino)-1,1-bis(phenylsulphonyl)-ethene; | VV |
| 1,1-bis(4-chlorophenylsulphonyl)-2-(pyrid-3-ylamino)ethene; | WW |
| 1,1-bis(4-chlorophenylsulphonyl)-2-(pyrid-4-ylamino)ethene; | XX |
| 1,1-bis(4-chlorophenylsulphonyl)-2-(4,6-dimethylpyrid-2-ylamino)ethene; | YY |
| 2-(5-trifluoromethylpyrid-2-ylamino)-1,1-bis(phenylsulphonyl)ethene; and | ZZ |
| 2-(3-methylpyrid-2-ylamino)-1,1-bis(phenyl-sulphonyl)ethene. | AAA |

Compounds C, H, J, K, V, X, Z, EE, XX and, especially, A and B are of particular importance.

The letters A to AAA are allocated to the compounds for easy reference later in the specification, e.g. in the table and in the Examples.

The compounds have valuable pharmacological properties, in particular properties which are indicative of outstanding utility in the treatment of arthritic disorders such as rheumatoid arthritis.

For example, in tests, compounds of formula I, when administered to mice orally at the doses shown in the following Table I, reduced by 50% the inhibition of migration of incubated mouse macrophage cells. This is a measure of inhibition or reduction of the levels of lymphokines and is indicative of utility in the treatment of arthritic patients.

TABLE 1

| Test Compound | oral dose (mg/kg animal body weight) |
|---|---|
| A | 2 |
| | 10 |
| | 20 |
| B | 12 |
| C | 11 |
| | 18 |
| H | 11 |
| J | 5 |
| | 7 |
| K | 35 |
| V | 37 |
| X | 37 |
| Z | 50 |
| EE | 10 |

TABLE 1-continued

| Test Compound | oral dose (mg/kg animal body weight) |
|---|---|
| XX | 35 |

Furthermore, in laboratory tests, the compounds have been shown to inhibit the deterioration of joints in the limbs of rabbits, cavies and rats. These results are particularly important because compounds currently employed in the treatment of arthritic disorders are primarily antiinflammatories and do not possess the said ability to inhibit joint deterioration.

The beneficial properties of the compounds of formula I are enhanced by the fact that they have only very low mammalian toxicity.

The compounds of formula I may be prepared by the application or adaptation of known methods.

Thus as a feature of the present invention, the compounds of formula I are prepared by the reaction of compounds of the general formula:

$$R^1-NH_2 \qquad \text{II}$$

(wherein $R^1$ is as hereinbefore defined) with compounds of the general formula:

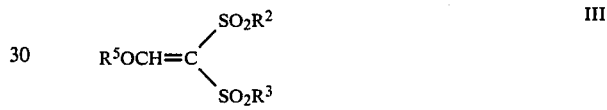

(wherein $R^2$ and $R^3$ are as hereinbefore defined and $R^5$ represents an alkyl group of 1 to 5 carbon atoms, preferably with a straight chain, e.g. ethyl), generally at temperatures between 0° and 250° C., preferably between 100° and 200° C., optionally in the presence of an inert solvent. Suitable inert solvents include aromatic hydrocarbons, e.g. toluene, aliphatic ethers, aliphatic nitriles and aliphatic amides, e.g. dimethylacetamide.

As will be evident to those skilled in the art, the process for the preparation of compounds of formula I by the reaction together of compounds of formulae II and III is liable to lead to mixtures of products if the value of one or more of the substituents $R^4$ is such that side reactions can occur, for example amino, hydroxy or alkylamino. In such circumstances it may be preferable to prepare the desired compound of formula I by the interconversion of another compound of formula I. For example, amino groups can be formed by reduction of nitro groups, hydroxy groups can be formed by the reduction of benzyloxy groups, and alkylamino groups can be formed by the reduction of N-benzyloxycarbonyl-N-alkylamino groups.

Thus, as a feature of the present invention, a compound of formula I wherein at least one of the substituents $R^4$ represents an amino, hydroxy or straight- or branched-chain alkylamino group containing from 1 to 6 carbon atoms, any other substituents being as hereinbefore defined, are prepared by the conversion of the corresponding compound of formula I wherein at least one of the substituents $R^4$ represents a nitro, benzyloxy or N-benzyloxycarbonyl-N-alkylamino group wherein the alkylamino moiety is straight- or branched-chain and contains from 1 to 6 carbon atoms, respectively, any other substituents being as hereinbefore defined. The reaction may be carried out by the application or adaptation of known methods, for example by hydrogenation in the presence of a hydrogenation catalyst, e.g. palladium on charcoal (e.g. 5–10% w/w), usually in an inert solvent such as a lower alkanol, e.g. ethanol, or dimethylformamide.

Compounds of formula III may be prepared by the application or adaptation of known methods, for example by the reaction of compounds of the general formula:

R²SO₂CH₂SO₂R³    IV (wherein R² and R³ are as hereinbefore defined) with compounds of the general formula:

CH(OR⁵)₃    V (wherein R⁵ is as hereinbefore defined) in the presence of a lower alkanoic anhydride and a catalyst such as zinc chloride or p-toluenesulphonic acid, at an elevated temperature (e.g. 140°–200° C.).

Compounds of the formulae II, IV and V may be prepared by the application or adaptation of known methods.

By the term "known methods" as used in this specification is meant methods heretofore used or described in the literature.

The following Examples illustrate the preparation of the compounds of the present invention.

EXAMPLE 1

Compounds A, B, C, D and E

A mixture of 2-amino-5-bromopyridine (38 g) and 1,1-bis(phenylsulphonyl)-2-ethoxyethene [70 g; prepared as described by Stetter et al, Monatshefte fur Chemie, 103, 1262–1270 (1972)] in toluene (1 liter) was slowly distilled during a period of 2 hours, maintaining the volume approximately constant by the gradual addition of further toluene to replace the liquid removed by the distillation. The mixture was then concentrated under vacuum and the residue was recrystallised twice from a mixture of chloroform and ethanol, to give 1,1-bis(phenylsulphonyl)-2-(5-bromopyrid-2-ylamino)ethene (80 g) m.p. 177°–179° C.

By proceeding in a similar manner, but replacing the 2-amino-5-bromopyridine, used as a starting material, by the appropriate quantities of:
2-aminopyridine;
2-amino-5-iodopyridine;
2-amino-5-dimethylaminopyridine; and
2-amino-5-piperidinopyridine;
respectively, and recrystallising the products from the solvents which are indicated after their melting points, there were prepared:

1,1-bis(phenylsulphonyl)-2-(pyrid-2-ylamino)ethene, m.p. 153°–156° C. (ethanol);

1,1-bis(phenylsulphonyl)-2-(5-iodopyrid-2-ylamino)ethene, m.p. 178°–181° C. (mixture of chloroform and methanol);

1,1-bis(phenylsulphonyl)-2-(5-dimethylaminopyrid-2-ylamino)ethene, m.p. 205°–207° C. (toluene); and 1,1-bis(phenylsulphonyl)-2-(5-piperidinopyrid-2-ylamino)ethene, m.p. 266°–268° C. (toluene).

EXAMPLE 2

Compounds F, G, H, I and J

An intimate mixture of 2-amino-5-nitropyridine (19.0 g) and 1,1-bis(phenylsulphonyl)-2-ethoxyethene (30 g) was heated at 180°–190° C. for 1 hour. After cooling, the solid cake was pulverised and recrystallised from a mixture of methyl ethyl ketone and methanol, to give 1,1-bis(phenylsulphonyl)-2-(5-nitropyrid-2-ylamino)ethene (28 g) m.p. 229°–231° C.

By proceeding in a similar manner, but replacing the 2-amino-5-nitropyridine, used as a starting material, by the appropriate quantities of:
2-amino-5-butylpyridine;
2-amino-5-cyanopyridine;
methyl 6-aminonicotinate; and
6-aminonicotinamide;
respectively, and recrystallising the products from the solvents which are indicated after their melting points, there were prepared:

1,1-bis(phenylsulphonyl)-2-(5-butylpyrid-2-ylamino)ethene, m.p. 203°–204° C. (mixture of chloroform and methanol);

1,1-bis(phenylsulphonyl)-2-(5-cyanopyrid-2-ylamino)ethene, m.p. 201°–204° C. (mixture of chloroform and methanol);

1,1-bis(phenylsulphonyl)-2-(5-methoxycarbonylpyrid-2-ylamino)ethene, m.p. 220°–221° C. (mixture of chloroform and methanol); and 1,1-bis(phenylsulphonyl)-2-(5-carbamoylpyrid-2-ylamino)ethene, m.p. 218°–219° C. (nitromethane)

EXAMPLE 3

Compound K

A mixture of 1,1-bis(phenylsulphonyl)-2-(5-nitropyrid-2-ylamino)ethene (2.23 g), concentrated hydrochloric acid (2 ml), palladium on charcoal catalyst (5% w/w; 1.5 g) and dimethylformamide (50 ml) was hydrogenated at 25° C. and atmospheric pressure until three molar equivalents of hydrogen had been taken up. After filtration to remove the catalyst, the dimethylformamide was removed under vacuum below 40° C. and the residue was treated with methanol (25 ml) and stirred for 30 minutes, and then allowed to stand for 24 hours. The resulting solid was then filtered off, dissolved in chloroform (25 ml), treated with anhydrous potassium carbonate (5 g), and stirred from 2 hours. The mixture was filtered, and the chloroform was removed in vacuo. The resulting residue was recrystallised from a mixture of acetonitrile and diethyl ether and dried thoroughly at 100° C./0.1 mmHg, to give 2-(5-aminopyrid-2-ylamino)-1,1-bis(phenylsulphonyl)ethene (0.5 g), m.p. 172°–174° C.

EXAMPLE 4

Compounds L, M, N, O, P, Q, R, S, T, U, V, W, X, Y and Z

A solution of 1-(3-chlorophenylsulphonyl)-2-ethoxy-1-phenylsulphonylethene (3.13 g) and 2-amino-5-bromopyridine (1.4 g) in dimethylacetamide (20 ml) was heated at reflux for 3.5 hours. The solution was cooled and poured onto ice (200 g), and the resulting pale yellow solid was filtered off and recrystallised from aqueous ehtaol (95% v/v), to give 2-(5-bromopyrid-2-ylamino)-1-(3-chloropheylsulphonyl)-1-phenylsulphonylethene (2.5 g), m.p. 170°–172° C.

By proceeding in a similar manner, but replacing the 1-(3-chlorophenylsulphonyl)-2-ethoxy-1-phenylsulphonylethene, used as a starting material, by the appropriate quantities of:

2-ethoxy-1-phenylsulphonyl-1-(3-trifluoromethyl-
    phenylsulphonyl)ethene;
2-ethoxy-1-(3-nitrophenylsulphonyl)-1-phenylsulphon-
    ylethene;
2-ethoxy-1-(3-methoxyphenylsulphonyl)-1-phenylsul-
    phonylethene;
2-ethoxy-1-(3-methylphenylsulphonyl)-1-phenylsul-
    phonylethene;
2-ethoxy-1-(2-methoxyphenylsulphonyl)-1-phenylsul-
    phonylethene;
2-ethoxy-1-(2-chlorophenylsulphonyl)-1-phenylsul-
    phonylethene;
2-ethoxy-1-(2-methylphenylsulphonyl)-1-phenylsul-
    phonylethene;
2-ethoxy-1,1-bis(3-nitrophenylsulphonyl)ethene;
1,1-bis(4-chlorophenylsulphonyl)-2-ethoxyethene;
1,1-bis(4-methoxyphenylsulphonyl)-2-ethoxyethene;
1,1-bis(4-methylphenylsulphonyl)-2-ethoxyethene;
1-(4-chlorophenylsulphonyl)-2-ethoxy-1-phenylsul-
    phonylethene;
2-ethoxy-1-(4-methylphenylsulphonyl)-1-phenylsul-
    phonylethene; and
2-ethoxy-1-(4-methoxyphenylsulphonyl)-1-phenylsul-
    phonylethene; respectively, there were prepared:
2-(5-bromopyrid-2-ylamino)-1-phenylsulphonyl-1-(3-trifluoromethylphenylsulphonyl)ethene, m.p. 155°–156° C. [recrystallised from aqueous ethanol (95% v/v)];
2-(5-bromopyrid-2-ylamino)-1-(3-nitrophenylsulphonyl)-1-phenylsulphonylethene, m.p. 174° C. [recrystallised from a mixture of ethanol and ethyl acetate];
2-(5-bromopyrid-2-ylamino)-1-(3methoxyphenylsulphonyl)-1-phenylsulphonylethene, m.p. 175°–177° C. [purified by medium pressure chromatography on silica gel, eluting with a mixture of toluene and ethyl acetate (19:1 v/v)];
2-(5-bromopyrid-2-ylamino)-1-(3-methylphenylsulphonly)-1-phenylsulphonylethene, m.p. 159°–160° C. [purified by medium presure chromatography on silica gel, eluting with chloroform, and recrystallised from a mixture of petroleum ether (b.p. 40°–60° C.) and ethyl acetate];
2-(5-bromopyrid-2-ylamino)-1-(2-methoxyphenylsulphonyl)-1-phenylsulphonylethene, m.p. 210°–211° C. [recrystallised from a mixture of ethyl acetate and ethanol];
2-(5-bromopyrid-2-ylamino)-1-(2-chlorophenylsulphonyl)-1-phenylsulphonylethene, m.p. 204°–206° C. [purified by medium pressure chromatography on silica gel, eluting with chloroform, and recrystallised from a mixture of acetone and ethyl acetate];
2-(5-bromopyrid-2-ylamino)-1-(2-methylphenylsulphonyl)-1-phenylsulphonylethene, m.p. 167°–169° C. [purified by medium pressure chromatography on silica gel, eluting with chloroform];
2-(5-bromopyrid-2-ylamino)-1,1-bis(3-nitrophenylsulphonyl)ethene, m.p. 172°–173° C. [extracted with ethyl acetate, dried over magnesium sulphate, evaporated to dryness, purified by medium pressure chromatography on silica gel with chloroform as eluant, and triturated with diethyl ether];
2-(5-bromopyrid-2-ylamino)-1,1-bis(4-chlorophneylsulphonyl)ethene, m.p. 232°–233° C. [recrystallised from ethanol];
2-(5-bromopyrid-2-ylamino)-1,1-bis(4-methoxyphenylsulphonyl)ethene, m.p. 180°–181° C. [purified by medium pressure chromatography on silica gel, eluting with a mixture of chloroform and ethyl acetate (4:1 v/v) and triturated with petroleum ether (b.p. 60°–80° C.)];

2-(5-bromopyrid-2-ylamino)-1,1-bis(4-methylphenylsulphonyl)ethene, m.p. 170°–172° C.;
2-(5-bromopyrid-2-ylamino)-1-(4-chlorophenylsulphonyl)-1-phenylsulphonylethene, m.p. 170°–171° C. [purified by medium pressure chromatography on silica gel, eluting with a mixture of chloroform and ethyl acetate (4:1 v/v) and recrystallising from ethanol];
2-(5-bromopyrid-2-ylamino)-1-(4-methylphenylsulphonly)-1-phenylsulphonylethene, m.p. 174°–176° C. [recrystallised from ethanol]; and
2-(5-bromopyrid-2-ylamino)-1-(4-methoxyphenylsulphonyl)-1-phenylsulphonylethene, m.p. 118°–119° C. [purified by medium pressure chromatography on silica gel, eluting with diethyl ether, and recrystallising from ethanol].

EXAMPLE 5

Compounds AA, BB, CC, DD, EE, FF, GG, HH, II, JJ, KK, LL, MM, NN, OO, PP, QQ, RR, SS, TT, UU and VV By proceeding in a manner similar to that described hereinbefore in Example 4, but replacing the 1-(3-chlorophenylsulphonyl)-2-ethoxy-1-phenylsulphonylethene, used as a starting material, by the appropriate quantity of 1,1-bis(phenylsulphonyl)-2-ethoxyethene, and replacing the 2-amino-5-bromopyridine, used as another starting material, by the appropriate quantities of:
2-amino-6-methyl-5-nitropyridine;
2-amino-4-methyl-3-nitropyridine;
3-amino-2-chloropyridine;
2-amino-5-sulphamoylpyridine;
2-amino-5-N,N-diethylsulphamoylpyridine;
2-amino-5-N-methylsulphamoylpyridine;
2-amino-5-N,N-diisopropylcarbamoylpyridine;
2-amino-5-thiocarbamoylpyridine (heating at reflux for only 15 minutes);
2-amino-5-N,N-diethylcarbamoylpyridine;
2-amino-5-N-butylcarbamoylpyridine;
2-amino-5-N-methylcarbamoylpyridine;
2-amino-5-N-phenylcarbamoylpyridine;
2-amino-5-piperidinocarbonylpyridine;
2-amino-4-methylpyridine;
2-amino-6-methylpyridine;
3-amino-4-methylpyridine;
2-amino-5-phenylthiopyridine;
3-amino-5-carbamoylpyridine;
2-amino-4-benzylpyridine;
2-amino-6-benzylpyridine;
3-amino-2-phenylthiopyridine; and
3-carbamoyl-6-amino-2-chloro-4-methyl-5-phenylpyridine;
respectively, there were prepared:
2-(6-methyl-5-nitropyrid-2-ylamino)-1,1-bis(phenylsulphonyl)ethene, m.p. 225°–226° C. [purified by extraction with dichloromethane, washing the extract with water, drying over magnesium sulphate and removal of solvents in vacuo, followed by medium pressure chromatography on silica gel, eluting with chloroform, and recrystallisation from ethyl acetate];
2-(4-methyl-3-nitropyrid-2-ylamino)-1,1-bis(phenylsulphonyl)ethene, m.p. 192°–195° C. [purified by medium pressure chromatography on silica gel, eluting with chloroform];
2-(2-chloropyrid-3-ylamino)-1,1-bis(phenylsulphonyl)ethene, m.p. 180°–182° C. [recrystallised from a mixture of petroleum ether (b.p. 60°-80° C.) and ethyl acetate];

1,1-bis(phenylsulphonyl)-2-(5-sulphamoylpyrid-2-ylamino)ethene, m.p. 249°-251° C. [purified by extraction with ethyl acetate, washing the extract with water, drying over magnesium sulphate and removal of solvents in vacuo, followed by medium pressure chromatography on silica gel, eluting with ethyl acetate];

2-(5-N,N-diethylsulphamoylpyrid-2-ylamino)-1,1-bis(phenylsulphonyl)ethene, m.p. 180°-190° C. [recrystallised from ethyl acetate];

2-(5-N-methylsulphamoylpyrid-2-ylamino)-1,1-bis(-phenylsulphonyl)ethene, m.p. 222°-223° C. [recrystallised from ethyl acetate]; p 2-(5-N,N-diisopropylcarbamoylpyrid-2-ylamino)-1,1-bis(phenylsulphonyl)ethene, m.p. 175°-176° C. [recrystallised from ethyl acetate];

2-(5-thiocarbamoylpyrid-2-ylamino)-1,1-bis(phenylsulphonyl)ethene (solvated with 0.5 moles ethanol per mole), m.p. 159°-162° C. with resolidification and a second melting point at 205°-206° C. (with decomposition) [purified by medium pressure chromatography on silica gel, eluting with chloroform, and recrystallised from a mixture of chloroform and ethanol];

2-(5-N,N-diethylcarbamoylpyrid-2-ylamino)-1,1-bis(-phenylsulphonyl)ethene, m.p. 154°-155° C. [purified by medium pressure chromatography on silica gel, eluting with ethyl acetate, and recrystallised from ethanol];

2-(5-N-butylcarbamoylpyrid-2-ylamino)-1,1-bis(-phenylsulphonyl)ethene (hydrate), m.p. 125°-130° C. with resolidification and a second melting point at 140°-141° C. [recrystallised from ethyl acetate];

2-(5-N-methylcarbamoylpyrid-2-ylamino)-1,1-bis(-phenylsulphonyl)ethene, m.p. 215°-216° C. [purified by medium pressure chromatography on silica gel, eluting with ethyl acetate, and recrystallised from ethanol];

1,1-bis(phenylsulphonyl)-2-(5-N-phenylcarbamoyl-pyrid-2-ylamino)ethene, m.p. 234°-236° C. (with decomposition) [recrystallised from ethyl acetate];

1,1-bis(phenylsulphonyl)-2-(5-piperidinocarbonylpy-rid-2-ylamino)ethene, m.p. 266°-268° C. [recrystallised from toluene];

2-(4-methylpyrid-2-ylamino)-1,1-bis(phenylsulphonyl)ethene, m.p. 168°-169° C. [recrystallised from ethanol];

2-(6-methylpyrid-2-ylamino)-1,1-bis(phenylsulphonyl)ethene (solvated with 0.5 moles ethanol per mole), m.p. 125°-130° C. with resolidification and a second melting point at 148°-149° C. [recrystallised from ethanol];

2-(4-methylpyrid-3-ylamino)-1,1-bis(phenylsulphonyl)ethene, m.p. 191°-192° C. [recrystallised from ethanol];

1,1-bis(phenylsulphonyl)-2-(5-phenylthiopyrid-2-ylamino)ethene, m.p. 144°-146° C. [recrystallised from ethanol];

2-(5-carbamoylpyrid-3-ylamino)-1,1-bis(phenylsulphonyl)ethene, m.p. 253°-254° C. [recrystallised from ethanol];

2-(4-benzylpyrid-2-ylamino)-1,1-bis(phenylsulphonyl)ethene, m.p. 137°-142° C. [recrystallised from ethanol];

2-(6-benzylpyrid-2-ylamino)-1,1-bis(phenylsulphonyl)ethene, m.p. 175° C. [purified by medium pressure chromatography on silica gel, eluting with chloroform, and recrystallised from ethyl acetate];

1,1-bis(phenylsulphonyl)-2-(2-phenylthiopyrid-3-ylamino)ethene, m.p. 160°-161° C. [purified by medium pressure chromatography on silica gel, eluting with ethyl acetate, and recrystallised from ethyl acetate]; and 2-(5-carbamoyl-6-chloro-4-methyl-3-phenylpyrid-2-ylamino)-1,1-bis(phenylsulphonyl)ethene, m.p. 244°-245° C. [recrystallised from ethyl acetate].

EXAMPLE 6

Compounds WW, XX and YY

By proceeding in a manner similar to that hereinbefore described in Example 4, but replacing the 1-(3-chlorophenylsulphonyl)-2-ethoxy-1-phenylsulphonyle-thene, used as a starting material, by the appropriate quantity of 1,1-bis(4-chlorophenylsulphonyl)-2-methox-yethene, and replacing the 2-amino-5-bromopyridine, used as another starting material, by the appropriate quantities of:
3-aminopyridine;
4-aminopyridine; and
2-amino-4,6-dimethylpyridine;
respectively, there were prepared:

1,1-bis(4-chlorophenylsulphonyl)-2-(pyrid-3-ylamino)ethene, m.p. 211°-212° C. [recrystallised from ethyl acetate];

1,1-bis(4-chlorophenylsulphonyl)-2-(pyrid-4-ylamino)ethene, m.p. 224°-225° C. (with decomposition) [purified by medium pressure chromatography on silica gel, eluting with ethyl acetate, and recrystallised from a mixture of petroleum ether (b.p. 40°-60° C.) and ethyl acetate]; and 1,1-bis(4-chlorophenylsulphonyl)-2-(4,6-dimethylpy-rid-2-ylamino)ethene, m.p. 199°-200° C. (with decomposition [purified by medium pressure chromatography on silica gel, eluting with chloroform, and recrystallised from a mixture of petroleum ether (b.p. 40°-60° C.) and ethyl acetate].

EXAMPLE 7

Compounds ZZ and AAA

By proceeding in a manner similar to that described hereinbefore in Example 1, but replacing the 2-amino-5-bromopyridine, used as a starting material, by the appropriate quantities of:
2-amino-5-trifluoromethylpyridine; and
2-amino-3-methylpyridine; respectively, there were prepared:

2-(5-trifluoromethylpyrid-2-ylamino)-1,1-bis(phenyl-sulphonyl)ethene, m.p. 175°-177° C. [recrystallised from toluene]; and 2-(3-methylpyrid-2-ylamino)-1,1-bis(phenylsul-phonyl)ethene, m.p. 169°-171° C. [recrystallised from a mixture of chloroform and ethanol].

The present invention includes within its scope pharmaceutical compositions which comprise at least one compound of formula I in association with a pharmaceutically acceptable carrier or coating. In clinical practice the compositions of the present invention will normally be administered orally or rectally, or parenterally, for example topically or intraarticularly.

Solid compositions for oral administration include compressed tablets, pills dispersible powders, and granules. In such solid compositions one or more of the active compounds is mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents.

The compositions according to the invention, for oral administration, also include capsules of absorbable material such as gelatin containing one or more of the active compounds with or without the addition of diluents or excipients.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in a sterile injectable medium immediately before use. As well as the more customary intravenous and intramuscular routes, the compositions may be administered by intra-articular injection.

Compositions in the form of solutions or suspensions, if desired together with additives as described above, in water or in vegetable or other greases, paraffin or other waxes, or lacquers or creams or lotions, to be applied topically, for example to the skin area around an affected joint to relieve arthritis, are also included in the invention. They may also include additives such as nicotinamide to assist absorption.

The percentages of active ingredient in the compositions of the invention may be varied, it being necessary that they should constitute a proportion such that a suitable dosage for the desired antiarthritic effect shall be obtained. Obviously several unit dosage forms may be administered at about the same time. Generally the compositions should contain 0.1% to 80% by weight of active ingredient, especially when in tablet form.

The dose employed depends upon the desired antiarthritic effect, the route of administration and the duration of the treatment. In the adult, the doses are generally between 0.01 and 100 mg (preferably between 0.1 and 10 mg) of the compounds of formula I per kg body weight per day.

The compounds of formula I may be administered each day or, according to the wishes of the medical practioner, less often, e.g. weekly.

The present invention provides a method of treating arthritic disorders in man which comprises administering to the patient an amount of a compound of formula I sufficient to combat an arthritic disorder.

The following Composition Example illustrates pharmaceutical compositions according to the present invention.

COMPOSITION EXAMPLE 1

Capsules for oral administration were made up in the usual manner by filling No. 2 size gelatin capsules each with 155 mg of the following composition:

| | |
|---|---|
| 1,1-bis(phenylsulphonyl)-2-(5-bromopyrid-2-ylamino)ethene | 50 mg |
| potato starch | 100 mg |
| magnesium stearate | 2.5 mg |
| Aerosil | 2.5 mg |

Similar compositions can be prepared by the use of any of the other compounds of formula I, for example compounds B to AAA hereinbefore identified.

We claim:

1. A pyridylaminoethene derivative of the formula:

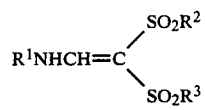

wherein $R^1$ represents a pyridyl group which is unsubstituted or substituted by one or more substituents $R^4$ (which may be the same or different and each represents a halogen atom or an amino, carboxy, cyano, nitro, hydroxy, formyl, trifluoromethyl, benzyloxycarbonylamino, sulphamoyl, tetrazol-5-yl, carbamoyl, or thiocarbamoyl group, or a straight- or branched-chain alkyl group containing from 1 to 6 carbon atoms, or a straight- or branched-chain alkoxy, alkylthio, alkylsulphonyl, alkylamino, or alkylsulphamoyl group containing from 1 to 6 carbon atoms in the alkyl moiety, a straight- or branched-chain alkanoyl, alkoxycarbonyl, alkoxycarbonylamino, alkylcarbamoyl or alkanoylamino group containing from 2 to 6 carbon atoms, an N-benzyloxycarbonyl-N-alkylamino group wherein the alkylamino moiety is straight- or branched-chain and contains from 1 to 6 carbon atoms, or a dialkylsulphamoyl, dialkylamino or dialkylcarbamoyl group wherein the alkyl moieties may be straight or branched and may each contain from 1 to 6 carbon atoms and may be linked together to form a ring or a phenyl, phenoxy, phenylthio, phenyloarbamoyl, benzoyl or phenylalkyl group, the phenyl groups of which may bear one or more substituents $R^4$ as hereinbefore defined) and $R^2$ and $R^3$ may be the same or different and each represents a phenyl group which may be unsubstituted or substituted by one or more substituents $R^4$ as hereinbefore defined.

2. A compound according to claim 1 wherein $R^1$ represents a pyridyl group, unsubstituted or substituted by one or more substituents $R^4$, and $R^2$ and $R^3$ each represents a phenyl group unsubstituted or substituted by one or more substituents $R^4$, the symbol $R^4$ being as defined in claim 1 with the exclusion of phenoxy, phenylthio, thiocarbamoyl, phenylcarbamoyl and phenylalkyl groups.

3. A compound according to claim 1 wherein $R^1$ represents a pyridyl group unsubstituted or substituted by 1, 2 or 4 substituents $R^4$.

4. A compound according to claim 1 wherein $R^1$ represents a pyridyl group unsubstituted or substituted by one substituent $R^4$.

5. A compound according to claim 1 wherein $R^1$ represents an unsubstituted or substituted pyrid-2-yl group.

6. A compound according to claim 1 wherein $R^4$ is selected from halogen atoms and amino, cyano, nitro, trifluoromethyl, phenyl, phenylthio, sulphamoyl, carbamoyl, thiocarbamoyl, phenylcarbamoyl, alkyl, alkylsulphamoyl, phenylalkyl, alkoxycarbonyl, alkylcarbamoyl, dialkylsulphamoyl, dialkylamino and dialkylcarbamoyl groups.

7. A compound according to claim 1 wherein $R^2$ and $R^3$, which may be the same or different represent unsubstituted phenyl or phenyl substituted by a halogen atom or by an alkyl, alkoxy, nitro or trifluoromethyl group.

8. A compound according to claim 7 wherein the halogen is chlorine, the alkyl group is methyl and the alkoxy group is methoxy.

9. A compound according to claim 1 which is 1,1-bis(phenylsulphonyl)-2-(5-bromopyrid-2-ylamino)ethene.

10. A compound according to claim 1 which is 1,1-bis(phenylsulphonyl)-2-(pyrid-2-ylamino)ethene.

11. A compound according to claim 1 which is 1,1-bis(phenylsulphonyl)-2-(5-iodopyrid-2-ylamino)ethene.

12. A compound according to claim 1 which is 1,1-bis(phenylsulphonyl)-2-(5-cyanopyrid-2-ylamino)ethene.

13. A compound according to claim 1 which is 1,1-bis(phenylsulphonyl)-2-(5-carbamoylpyrid-2-ylamino)ethene.

14. A compound according to claim 1 which is 2-(5-aminopyrid-2-ylamino)-1,1-bis(phenylsulphonyl)ethene.

15. A compound according to claim 1 which is 2-(5-bromopyrid-2-ylamino)-1,1-bis(4-methoxyphenylsulphonyl)ethene.

16. A compound according to claim 1 which is 2-(5-bromopyrid-2-ylamino)-1-(4-chlorophenylsulphonyl)-1-phenylsulphonylethene.

17. A compound according to claim 1 which is 2-(5-bromopyrid-2-ylamino)-1-(4-methoxyphenylsulphonyl)-1-phenylsulphonylethene.

18. A compound according to claim 1 which is 2-(5-N,N-diethylsulphamoylpyrid-2-ylamino)-1,1-bis(-phenylsulphonyl)ethene.

19. A compound according to claim 1 which is 1,1-bis(4-chlorophenylsulphonyl)-2-(pyrid-4-ylamino)ethene.

20. A compound according to claim 1 which is 1,1-bis(phenylsulphonyl)-2-(5-dimethylamino-pyrid-2-ylamino)ethene; 1,1-bis(phenylsulphonyl)-2-(5-piperidinopyrid-2-ylamino)ethene; 1,1-bis(phenylsulphonyl)-2-(5-nitropyrid-2-ylamino)ethene; 1,1-bis(-phenylsulphonyl)-2-(5-butylpyrid-2-ylamino)ethene; or 1,1-bis(phenylsulphonyl)-2-(5-methoxycarbonyl-pyrid-2-ylamino)ethene.

21. A compound according to claim 1 which is 2-(5-bromopyrid-2-ylamino)-1-(3-chlorophenylsulphonyl)-1-phenylsulphonylethene; 2-(5-bromopyrid-2-ylamino)-1-phenylsulphonyl-1-(3-trifluoromethylphenylsulphonyl)ethene; 2-(5-bromopyrid-2-ylamino)-1-(3-nitrophenylsulphonyl)-1-phenylsulphonylethene; 2-(5-bromopyrid-2-ylamino)-1-(3-methoxyphenylsulphonyl)-1-phenylsulphonylethene; 2-(5-bromopyrid-2-ylamino)-1-(3-methylphenylsulphonyl)-1-phenylsulphonylethene; 2-(5-bromopyrid-2-ylamino)-1-(2-methoxyphenylsulphonyl)-1-phenylsulphonylethene; 2-(5-bromopyrid-2-ylamino)-1-(2-chlorophenylsulphonyl)-1-phenylsulphonylethene; 2-(5-bromopyrid-2-ylamino)-1-(2-methylphenylsulphonyl)-1-phenylsulphonylethene; 2-(5-bromopyrid-2-ylamino)-1,1-bis(3-nitro-phenylsulphonyl)ethene; 2-(5-bromopyrid-2-ylamino)-1,1-bis(4-chlorophenylsulphonyl)ethene; 2-(5-bromopyrid-2-ylamino)-1,1-bis(4-methyl-phenylsulphonyl)ethene; 2-(5-bromopyrid-2-ylamino)-1-(4-methylphenyl-sulphonyl)-1-phenylsulphonylethene; 2-(6-methyl-5-nitropyrid-2-ylamino)-1,1-bis-(phenylsulphonyl)ethene; 2-(4-methyl-3-nitropyrid-2-ylamino)-1,1-bis-(phenylsulphonyl)ethene; 2-(2-chloropyrid-3-ylamino)-1,1-bis(phenylsulphonyl)ethene; 1,1-bis(-phenylsulphonyl)-2-(5-sulphamoylpyrid-2-ylamino)ethene; 2-(5-N-methylsulphamoylpyrid-2-ylamino)-1,1-bis(phenylsulphonyl)ethene; 2-(5-N,N-diisopropylcarbamoylpyrid-2-ylamino)-1,1-bis(phenylsulphonyl)ethene; 2-(5-thiocarbamoylpyrid-2-ylamino)-1,1-bis(-phenylsulphonyl)ethene; 2-(5-N,N-diethylcarbamoylpyrid-2-ylamino)-1,1-bis(phenylsulphonyl)ethene; 2-(5-N-butylcarbamoylpyrid-2-ylamino)-1,1-bis(phenylsulphonyl)ethene; 2-(5-N-methylcarbamoylpyrid-2-ylamino)-1,1-bis-(phenylsulphonyl)ethene; 1,1-bis(-phenylsulphonyl)-2-(5-N-phenylcarbamoylpyrid-2-ylamino)ethene; 1,1-bis(phenylsulphonyl)-2-(5-piperidino-carbonylpyrid-2-ylamino)ethene; 2-(4-methylpyrid-2-ylamino)-1,1-bis(phenylsulphonyl)ethene; 2-(6-methylpyrid-2-ylamino)-1,1-bis(phenylsulphonyl)ethene; 2-(4-methylpyrid-3-ylamino-1,1-bis(phenylsulphonyl)ethene; 1,1-bis(phenylsulphonyl)-2-(5-phenylthiopyrid-2-ylamino)ethene; 2-(5-carbamoylpyrid-3-ylamino)-1,1-bis(phenylsulphonyl)ethene; 2-(4-benzylpyrid-2-ylamino)-1,1-bis(phenylsulphonyl)ethene; 2-(6-benzylpyrid-2-ylamino)-1,1-bis(phenylsulphonyl)ethene; 1,1-bis(phenylsulphonyl)-2-(2-phenylthiopyrid-3-ylamino)ethene; 2-(5-carbamoyl-6-chloro-4-methyl-3-phenylpyrid-2-ylamino)-1,1-bis(phenylsulphonyl)ethene; 1,1-bis(4-chlorophenylsulphonyl)-2-(pyrid-3-ylamino)ethene; 1,1-bis(4-chlorophenylsulphonyl)-2-(4,6-dimethylpyrid-2-ylamino)ethene; 2-(5-trifluoromethylpyrid-2-ylamino)-1,1-bis(phenylsulphonyl)ethene; or 2-(3-methylpyrid-2-ylamino)-1,1-bis(-phenylsulphonyl)ethene.

22. A pharmaceutical composition useful in the treatment of arthritic disorders which comprises, as active ingredient, an amount of a pyridylaminoethene derivative as claimed in claim 1 effective to combat the disorder, in association with a pharmaceutically acceptable carrier or coating.

23. A method for the treatment of a patient suffering from an arthritic disorder which comprises administering to the patient an amount of a pyridylaminoethene derivative as claimed in claim 1 effective to combat the disorder.

* * * * *